(12) United States Patent
Stübinger et al.

(10) Patent No.: US 11,045,321 B2
(45) Date of Patent: Jun. 29, 2021

(54) METHOD FOR PROVIDING SUB-ELEMENTS OF A MULTIPART IMPLANT OR A MULTIPART OSTEOSYNTHESIS

(71) Applicant: UNIVERSITÄT BASEL VIZEREKTORAT FORSCHUNG, Basel (CH)

(72) Inventors: Stefan Stübinger, Binningen (CH); Timo Zillig, Rheinfelden (CH)

(73) Assignee: UNIVERSITÄT BASEL, Basel (CH)

( * ) Notice: Subject to any disclaimer, the term of this patent is extended or adjusted under 35 U.S.C. 154(b) by 175 days.

(21) Appl. No.: 16/083,627

(22) PCT Filed: Mar. 10, 2017

(86) PCT No.: PCT/EP2017/055640
§ 371 (c)(1),
(2) Date: Sep. 10, 2018

(87) PCT Pub. No.: WO2017/153560
PCT Pub. Date: Sep. 14, 2017

(65) Prior Publication Data
US 2019/0380836 A1    Dec. 19, 2019

(30) Foreign Application Priority Data
Mar. 11, 2016    (EP) ..................... 16159953

(51) Int. Cl.
*A61F 2/28*    (2006.01)
*A61F 2/30*    (2006.01)

(52) U.S. Cl.
CPC ............ *A61F 2/28* (2013.01); *A61F 2/30942* (2013.01); *A61F 2002/3096* (2013.01);
(Continued)

(58) Field of Classification Search
CPC .. A61F 2/28; A61F 2/2803; A61F 2002/2807; A61F 2002/30955
See application file for complete search history.

(56) References Cited

U.S. PATENT DOCUMENTS 3,488,779 A * 1/1970 Christensen .......... A61F 2/3099
                                                  623/16.11
5,496,371 A * 3/1996 Eppley ................ A61F 2/30721
                                                  623/17.18
(Continued)

FOREIGN PATENT DOCUMENTS

WO    2008051967 A2    5/2008

OTHER PUBLICATIONS

International Preliminary Report on Patentability dated Sep. 20, 2018 in related International Application No. PCT/EP2017/055640 (all cited references were previously submitted in an IDS filed on Sep. 10, 2018).

(Continued)

*Primary Examiner* — Bruce E Snow
*Assistant Examiner* — Melissa A Hoban
(74) *Attorney, Agent, or Firm* — Patent Portfolio Builders PLLC

(57) ABSTRACT

A method for providing sub-elements of a multipart implant or a multi-part osteosynthesis prior to introducing same into a human and/or animal body, involves: A) detecting data of a patient for whom the implant and/or the osteosynthesis is intended; B) generating a model using the detected data; C) generating manufacture specifications for at least two or more sub-elements which can be combined so as to form an implant and/or an osteosynthesis on the basis of the generated model, said manufacture specifications comprising C1) a dimensioning of the sub-elements; and D) manufacturing the sub-elements on the basis of the manufacture specifica- (Continued)

tions. The sub-elements can be assembled together so as to form an implant or an osteosynthesis.

16 Claims, 7 Drawing Sheets

(52) U.S. Cl.
CPC ............... *A61F 2002/30948* (2013.01); *A61F 2002/30955* (2013.01); *A61F 2002/30962* (2013.01); *A61F 2250/0007* (2013.01); *A61F 2310/00023* (2013.01)

(56) References Cited

U.S. PATENT DOCUMENTS

| | | | | |
|---|---|---|---|---|
| 5,554,194 | A * | 9/1996 | Sanders | A61F 2/2875 623/17.17 |
| 6,060,641 | A | 5/2000 | Manolidis | |
| 9,226,828 | B2 * | 1/2016 | Bonutti | A61B 17/0218 |
| 2002/0007294 | A1 * | 1/2002 | Bradbury | G06F 19/3418 705/2 |
| 2006/0224242 | A1 * | 10/2006 | Swords | A61B 17/8085 623/17.19 |
| 2006/0241776 | A1 * | 10/2006 | Brown | A61B 17/7225 623/20.16 |
| 2007/0118243 | A1 * | 5/2007 | Schroeder | A61B 17/8061 700/118 |
| 2008/0097445 | A1 * | 4/2008 | Weinstein | A61B 17/8023 606/281 |
| 2011/0029093 | A1 * | 2/2011 | Bojarski | A61F 2/3859 623/20.35 |
| 2012/0330427 | A1 * | 12/2012 | Yaremchuk | A61F 2/0059 623/17.18 |
| 2013/0289727 | A1 | 10/2013 | Rudnick et al. | |
| 2014/0316526 | A1 * | 10/2014 | Grotz | A61F 2/3859 623/20.17 |
| 2015/0018829 | A1 | 1/2015 | Woodburn et al. | |
| 2015/0088142 | A1 | 3/2015 | Gibson | |
| 2017/0014169 | A1 * | 1/2017 | Dean | A61B 17/8071 |
| 2017/0296243 | A1 * | 10/2017 | Dunaway | A61F 2/30942 |
| 2018/0344464 | A1 * | 12/2018 | Engstrand | A61B 17/8085 |

OTHER PUBLICATIONS

International Search Report dated Jun. 2, 2017 in related International Application No. PCT/EP2017/055640.

Search Report dated Sep. 15, 2016 in related EP Application No. 16159953.5.

Written Opinion dated Jun. 2, 2017 in related International Application No. PCT/EP2017/055640.

* cited by examiner

METHOD FOR PROVIDING SUB-ELEMENTS OF A MULTIPART IMPLANT OR A MULTIPART OSTEOSYNTHESIS

BACKGROUND AND SUMMARY OF THE INVENTION

Exemplary embodiments of the present invention relate to a method for providing subelements of a multipart implant or a multipart osteosynthesis and a multipart implant and/or a multipart osteosynthesis.

Multipart implants are known from U.S. Pat. No. 6,060,641 A1, US 2015/0018829 A1, and WO 2008/051967 A2. They are composed of multiple individual parts and are arranged partially flexibly and partially rigidly along a skeleton. This has the disadvantage that these implants are not specifically tailored to the patient. The implants are variable in their size by removing or adding subelements, however, this always takes place only within the limits predefined by the dimensioning of the respective subelements. Such implants are thus not ideally adapted to the individual patients, but rather are always slightly too large or slightly too small depending on the number of the subelements.

US 2012/003427 A1 discloses a multipart implant, for example, two sections of a jaw, which are connected to one another via a plug connection. They have fittings for positioning on and/or above a chin bone fracture and are used to stabilize this bone. A dimensioning of connecting means of the same type based on the thickness of a bone can be performed on the basis of a CT scan. The CT scan is only used in this case for the surface analysis of the bone and for manufacturing a support rail individually adapted to the patient to support the bone. The use of a CT scan therefore extends to the manufacturing of surface-adapted patient-individualized support rails and the dimensioning of the connecting means between the support rails. The material of the support rails can be polyethylene material or biocompatible material in this case.

US 2013/0289727 A uses a CT scan for dimensioning implantation plates. The type of the connecting means between the implantation plates is an overlapping flange in this case, which is fixed by means of a fastening means. The material of the plates is always the same in this case.

To enable an optimum seat of an implant and/or a skeleton, exemplary embodiments of the present invention provide a method, using which an implant individually adapted to the patient or an osteosynthesis individually adapted to the patient can be manufactured.

A method according to the invention for providing subelements of a multipart implant or a multipart osteosynthesis before the introduction thereof into a human and/or animal body comprises the following steps:

A) acquiring data of a patient, for which the implant and/or the osteosynthesis is intended;

An osteosynthesis is to be understood as the entirety of connecting means of a connection, which can be used between two or more bones or bone fragments with the goal that they grow together.

These data can preferably be recordings of an imaging method. These recordings of imaging methods are typically used for diagnosis. However, in the present case these recordings are produced to produce a model independently of a diagnosis or alternatively are used further after completed diagnosis.

B) producing a model on the basis of the acquired data;

The production of the model can be performed as a computer model. A computer program, which is based on the finite element method, can preferably be used for this purpose. Corresponding computer programs are already commercially available for other applications and merely have to be reconfigured in a manner known per se for the application.

C) producing manufacturing specifications for at least two or more subelements that can be assembled to form an implant and/or an osteosynthesis on the basis of the produced model, wherein the manufacturing specifications comprise:

C1) a dimensioning of the subelements

The manufacturing specifications are preferably produced based on the computer model such that the subelements are dimensioned differently depending on the function thereof. A bone plate is also somewhat thicker at one point than at another. The required material thickness and flexibility of the subelements can be individually designed and manufactured by the model, which is based on patient-specific data.

D) manufacturing the subelements based on the manufacturing specifications, wherein the subelements can be assembled with one another to form an implant or an osteosynthesis.

The step of manufacturing subelements can also comprise the adaptation of prefinished elements, for example, grinding down of a preform on the basis of a patient-specific manufacturing specification.

Detached from the subsequent surgical intervention for the introduction, the method according to the invention relates to the provision of subelements, which can be assembled to form an implant adapted to the patient or a corresponding osteosynthesis.

Due to the multipart nature of the implant or the osteosynthesis and/or connection, the surgical intervention can take place in a minimally invasive manner and the space requirement and the functionality of the implant are particularly optimized by the patient-specific adaptation.

The production of manufacturing specifications for at least two or more subelements that can be assembled to form an implant and/or an osteosynthesis is performed on the basis of the produced model, wherein the manufacturing specifications comprise the following further specifications:

C2) a material selection with respect to one or more materials for a respective subelement;

This enables an optimum tailoring with respect to a desired flexibility or rigidity of the subelements.

C3) a selection of one or more connection types between the respective subelements.

An optimum connection can thus be achieved for each subelement depending on the physical region. In this case, a high weight per unit area or elevated tensile stress can act on the connection depending on the physical region. The connection can be selected accordingly.

In the prior art, selection according to connection types or a material selection has heretofore not taken place on the basis of the acquired data, in particular a CT scan.

A connection type in the scope of the present invention is not to be understood as the selection of connecting means of the same type of different dimensioning, but rather the ranges of the force transmission between the connecting means differ depending on the connection type. One connection type can thus have wide undercuts, for example, in the form of dovetail connections, while in contrast other connection types have threads.

These specifications improve the application performance of the implant or the osteosynthesis and/or the connection.

The subelements can advantageously be connectable to one another in a formfitting manner or can be spaced apart from one another at least regionally at a predefined spacing. The first is particularly preferable for enabling solid bonding and a wide surface contact. The spacing can, in contrast, be used for anchoring tissue, which additionally supports the connection.

The manufacturing specifications can moreover comprise a selection of one or more sensors, actuators, and/or active ingredients for at least one of the subelements. The implant thus enables additional monitoring of the health status of the patient.

An integration and/or fixation of a power supply source and/or a control and/or analysis unit on or in one of the subelements can take place during the manufacturing of the subelements for the operation and/or the analysis of the sensor signals and/or for controlling and/or actuating the actuators.

Moreover, a transmitting unit can advantageously be arranged on or in the implant or the osteosynthesis during the manufacturing. The transmitting unit can be an active or passive transmitting unit.

The production of the model can advantageously be performed by producing a three-dimensional computer model, preferably according to the finite element method.

The acquisition of data can advantageously be performed by an imaging method for the purpose of producing a three-dimensional model.

The acquisition of the data according to step A) takes place on the basis of one of the CT scans of the individual patient.

A model for the individual implant planning can be produced on the basis of the CT scan, wherein the geometry of the model of an implant including locally varying individual material thicknesses and individually-distributed types of material is acquired on the basis of the CT scan. For example, the mechanical carrying capacity of every scanned region, for example, in relation to compression, tension, or transverse forces, can be determined by the CT scan, as well as the varying bone thickness distribution in the respective scanned region.

A differentiation between skin and bone can also be performed, and therefore subelements having tissue components can be taken into consideration during the implant planning.

A production of the model that takes into consideration the different material parameters and material limits, in particular the material thickness, the material yield strength, the material breaking point, in particular in the case of mechanical load from different directions, and/or the material elasticity of subsections of the implant can then advantageously preferably be performed on the basis of the CT scan.

The selection of the type of the connection of individual subelements then takes place as a function of individual load cases on the subelement on the basis of the model. Multiple connection types are available in this case, which enable a different mechanical connection of the subelements depending on the load case, for example, depending on transverse forces on the connection. A dovetail connection thus occupies a very wide connection and can have a high resistance force even in the event of transverse forces transversely but not perpendicularly to the connection direction. The concept of the transverse forces is also to be understood accordingly hereafter in the scope of the present invention. In contrast, a plug connection by attachment pins has a low resistance in relation to transverse forces, which can result in breaking off of the pin connection.

In contrast to the prior art, the subelements are individually adapted at least in the region of the outer contour of the implant or the osteosynthesis. Therefore, advantageously at least 66% of all subelements are manufactured differently dimensioned from one another and particularly preferably at least 80% of all subelements are manufactured differently dimensioned from one another. In the prior art, usually only two types of subelements are provided in multipart implants, i.e., 50% of all subelements are identically dimensioned. This enables a particularly small-part and individualized adaptation.

The subelements in the assembled state of an implant and/or an osteosynthesis advantageously define an edge model having a larger volume than each individual subelement, preferably an edge model three times larger.

The subelements in the assembled state of the implant and/or the osteosynthesis can advantageously define an edge model having a volume at least eight times larger than each individual subelement. The increased number of subelements enables better and more patient-specific concept planning of the material requirements in specific subregions of the implant. Large-part subelements having a variety of different materials, for example, for bones, artificial tissue parts, and/or artificial muscles, are therefore not complexly arranged on a large subelement, but rather in particular structurally difficult portions can be prefinished more easily because of the subdivision into multiple subelements.

The subelements preferably comprise different materials because of their different functionality. In one advantageous embodiment variant, a first subelement of the subelements is thus manufactured from a first material and/or a first material combination and a second subelement of the subelements is manufactured from a second material and/or a second material combination. A first material combination can be, for example, rubber and titanium as a composite element and a second material combination can be PLA and titanium or also only pure titanium.

The density averaged to the volume and/or modulus of elasticity averaged to the volume of the first material and/or the first material combination is greater in this case than the density averaged to the volume and/or the modulus of elasticity averaged to the volume of the second material combination. This means that the density and/or the modulus of elasticity of the rubber is ascertained and this value is multiplied by the percentage volume proportion of this material in the subelement. The two values can then be added and scaled to 100% and can then be compared to the corresponding value of the material or the material combination of the second subelement. The first and/or second material combination also has to differ in this case only with respect to the proportion of the individual components in the material combination, for example, with respect to the proportion of rubber or titanium. The modulus of elasticity and/or the density and/or the volume of the material components can be ascertained under standard conditions using routine measuring devices in the technical field in consideration of the typical ranges of variation. The verification of the volume can be determined by measurement, possibly with the aid of a laser-assisted scanning method. The density of the implants or individual subelements can be ascertained by radiological determination, for example, by means of CT, for example, by the device Somatom Flash from Siemens. The elasticity of the subelements of the implant or the osteosynthesis, in particular also the tissue components, can be verified by means of the measuring device Bioindenter on the CSEM. The subelements can be adapted very individually to the situation of the patient by the different densities and moduli of elasticity.

A model—predominantly the bony structures—of the head is produced for the individual implant planning on the basis of the CT scan. This model is adapted in a further step into a corresponding FE model (FE=finite elements), in which the different tissue structures and also the implant can be considered and simulated under biomechanical aspects. For this purpose, the geometry of the structures/implant is volumetrically cross-linked. In this case, the division of the implant and the different material parameters and material limits is taken into consideration during the cross-linking. On the basis of these preparation steps, statements can be made with respect to the stability/material limits of the implant and the connection types based on individual load cases by means of simulation.

In this case, it is particularly advantageous if a first subelement of the subelements is manufactured from a first material and/or a first material combination, for example, a composite material, and a second subelement of the subelements is manufactured from a second material and/or a second material combination, wherein the density averaged to the volume and/or the modulus of elasticity averaged to the volume of the first material and/or the first material combination is greater, preferably at least 1.2 times greater, particularly preferably at least 1.5 times greater, than the density averaged to the volume and/or the modulus of elasticity averaged to the volume of the second material and/or the second material combination.

Alternatively or additionally, a subelement can be manufactured from a first material and from a second material, wherein the density and/or the modulus of elasticity of the first material is advantageously greater, preferably at least 1.2 times greater, particular preferably at least 1.5 times greater than the density and/or the modulus of elasticity of the second material.

The actuator or actuators and/or the sensor or the sensors of one or more subelements are preferably and advantageously formed in MEMS construction and the sensor elements and/or actuator elements, without analysis unit and/or power supply unit, are particularly preferably smaller than 1 mm$^3$.

One or more subelements can advantageously consist of a resorbable material and particularly preferably of a resorbable plastic or magnesium. These enable an assisting but not permanent buildup of body parts.

For simple installation, it is advantageous if the connections of the subelements are designed as plug connections. These plug connections can particularly preferably have an additional locking mechanism, which locks the subelements to one another after they are plugged together. Alternatively and also advantageously, the subelements can be connected to one another via a film hinge or an adhesive bond.

Furthermore, a multipart implant and/or multipart osteosynthesis, which is produced according to a method according to the invention, is according to the invention.

An endogenous element can advantageously be regionally or completely replaced by the implant or the osteosynthesis. For this purpose, the implant has an attachment face for attachment to a prefinished cut face. This cut face can be provided by a preparatory step, which is not according to the invention, however, of severing a fracture segment in the body. The implant or the osteosynthesis is therefore not used for stabilization of a bone but rather as its replacement in this preferred embodiment variant.

BRIEF DESCRIPTION OF THE DRAWING FIGURES

The present invention will be explained in greater detail on the basis of multiple exemplary embodiments and with the aid of the appended figures. In the figures.

DETAILED DESCRIPTION

Figure 5:
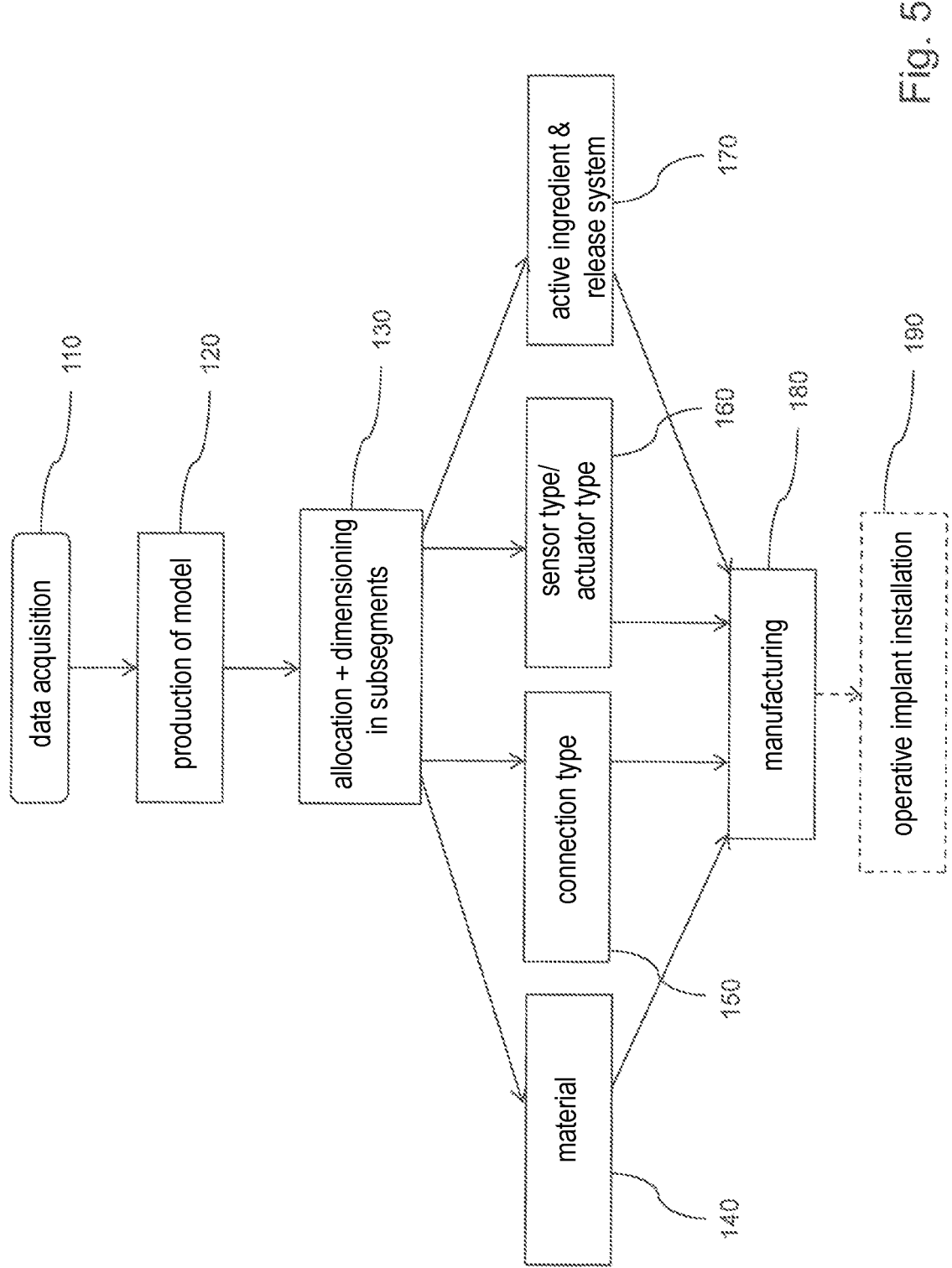
FIG. 5 shows a flow chart of a method according to the invention for providing a multipart implant or a multipart osteosynthesis.

FIG. 5 shows a method sequence of a method according to the invention for providing a multipart implant or a multipart osteosynthesis.

A data acquisition 110 takes place in a first step. This data acquisition is an individual data acquisition of a patient. It therefore relates to individual patient data, which were preferably produced on the basis of image production methods or imaging methods.

Such methods enable the recording of organs and/or bones, on the basis of which a model can subsequently be produced. Imaging methods are preferably based on the following signals, from which an image of individual organs, bones, or the like can subsequently be produced for the nuclear patient:
  nuclear magnetic resonance, for example, MRI scans,
  ultrasound, for example, sonographic scans,
  x-rays, for example, x-ray images,
  infrared radiation, for example, thermographic recordings,
  light in the visible range, for example, endoscopic recordings,
  impedance, for example, EIT recordings,
  radionuclides, for example, scintigraphic recordings.

Three-dimensional recordings of imaging methods are particularly preferred, and therefore imaging methods are preferred for data acquisition that enable three-dimensional recordings.

In addition to acquiring three-dimensional recordings, an acquisition of further chemical and/or physical data can also take place. This can comprise, for example, the acquisition of the concentration of specific compounds in the body, for example, an ion concentration and/or the pH value, the body temperature, the heart rate, and/or the contraction and expansion volume of individual organs. These values are partially also patient-specific.

On the basis of this data acquisition, a model 120 of an affected organ and/or an affected bone and/or the surroundings of the organ and/or bone can be produced. If the model involves the surroundings, a space requirement of the required implant and/or the required osteosynthesis can thus be ascertained on the basis of this model.

The model 120 can be a digital three-dimensional computer module or a real three-dimensional computer module, which was preferably produced by stereolithography, particularly preferably by rapid prototyping, and in particular by a generative manufacturing method, for example, selective laser melting or by 3D printing.

On the basis of this model 120, manufacturing specifications are produced before the design of the implant and/or the osteosynthesis, these specifications comprise, inter alia, an allocation and dimensioning 130 of individual parts or subelements of the three-dimensional individualized implant or the three-dimensional individualized osteosynthesis.

The model 120 and the subelements of the model can each be delimited by an imaginary cuboid edge model to define the three-dimensional extension thereof, wherein these edge models have the maximum extension of the model 120 and the maximum extension of the subelements. Each of the subelements is therefore smaller than the overall construct of the implant and/or the osteosynthesis.

In this case, the volume of the edge model delimiting the model 120 of the implant or the osteosynthesis is greater than the volume of the edge model which delimits a sub-element of the model 120.

The volume of the edge model of the model 120 is preferably at least three times larger, particularly preferably at least eight times larger than the volume of the edge model of the subelement of the model 120.

At least the cross-sectional area of a subelement particularly preferably has a smaller surface area than the cross-sectional area of the implant or the osteosynthesis containing the cross-sectional area of the subelement. This means that the cross-section of the implant or the osteosynthesis is larger at the height of the cross-section of the subelement than that of the subelement, preferably at least twice as large, particularly preferably at least four times as large.

The definition according to edge model relates in this case to a model of the implant and/or the osteosynthesis. If the model is a model of the surroundings, the three-dimensional space requirement of the required implant or the required osteosynthesis is thus to be produced on the basis of the model and the edge model is to be produced on the basis of this space requirement.

The macro-design of the implant to be provided or the osteosynthesis to be provided is coordinated by the model 120, which implant and/or which osteosynthesis is therefore adapted individually and optimally in all three spatial directions to the patient. The dimensions of the model and the implant or the osteosynthesis modeled according to the specifications of the model typically change in this case for every patient in all three spatial directions.

After the allocation of the model into subelements 130, a segment-specific selection is performed for the design with respect to a respective subelement.

This selection relates, inter alia, to the selection of the material 140 of a respective subelement and the selection of the connection 150 of the subelements to one another.

The material selection 140 can particularly preferably comprise one or more of the following materials: shape-memory material, self-assembly material, gradient material, artificial muscles and/or tissue components, preferably skin, mucosal membrane, periosteum, and/or soft tissue.

Shape-memory materials can preferably consist of plastic or an alloy, a so-called shape-memory alloy.

Self-assembly materials are materials, for example, which display a specific structure and pattern formation autonomously, i.e., without external actions. Moreover, however, they can also assume a new shape under excitation, for example, light, mechanical excitation, or electrical excitation. This can be, for example, a structure having rigid subregions, which are connected by film hinges and which can be introduced in a minimally-invasive manner into a wound and can subsequently be unfolded. The unfolding can preferably take place into a predefined shape.

Gradient materials are presently being studied and developed by the Fraunhofer Institute. One gradient material is, for example, PCU (polycarbonate urethane).

Artificial muscles are presently being studied, inter alia, under the project "Bionicum" in various research institutes. Such muscles also come into consideration for the material selection of the subelements.

Furthermore, cultivating tissue, in particular human tissue, is also known. This tissue can also be used as a material for the subelements. The tissue includes, inter alia, skin, mucosal membrane, periosteum, and soft tissue. As an alternative to the cultivation, the tissue can also be taken from the patient or a donor, human or animal, and taken into consideration in the material selection.

The selection of the connection types can advantageously take place such that at least the selection selects between the connection types of a dovetail connection, a male connector connection, and/or a joint connection, in particular a ball-joint head connection during the implant planning, for example, by a computer program. At least these three connection types are available as a data set during the planning. In the scope of the present invention, in particular male connector connections in which the pin has a pinhead which protrudes as a ball or another type of projection in relation to the pin shaft at the terminal position of the pin are to be understood as male connector connections.

In addition, further preferred materials for the material selection are materials having solid-liquid or solid-solid phase transformations under the influence of heat in the temperature range between 0 to 85° C. or the influence of light, graphene materials, magnetic materials, material combinations having different x-ray opacity, thermally-conductive materials, or electrically-conductive materials.

Both metals/alloys and also ceramic materials and/or plastics can be used in the material selection of the base material. In one preferred embodiment variant of the invention, in particular fiber-reinforced plastics can be used for producing the subelements, for example, carbon-reinforced polyether ether ketone (PEEK). Material combinations and material composites are also possible which can occur in a subelement. Depending on the stress of the implant and/or the osteosynthesis, it can occur that a first subelement is made particularly flexible and a second subelement of the same implant or the same osteosynthesis is particularly flexible, i.e., bendable and/or extensible and/or foam-type. This can be determined beforehand and adapted by the material selection. Every patient has different physical dimension and muscle forms in this case, and therefore the dimensioning of the implant or the osteosynthesis can be performed individually on the basis of the previously produced model.

Particularly preferably used metals are steel and/or titanium.

The preferred ceramic materials also include in particular materials made of magnesium.

Particularly preferably used plastics are resorbable plastics, preferably based on polylactic acid and/or the derivatives thereof, for example, PLA. The plastics can preferably be at least regionally fiber-reinforced.

This also applies to the selection of the type of the connection between the subelements. The connection can be partially flexible. This can be achieved via ball-and-socket joints, as are disclosed, for example, in U.S. Pat. No. 6,060,641 A. However, they can also be rigid. Various connection types are shown in greater detail in FIGS. 1-4. The present invention differs between connecting means, which connect subelements of the implant or the osteosynthesis to one another, and fixation means, which fix the implant or the osteosynthesis on an existing structure, for example, a skeleton in the body. However, the connecting means can also be used as fixation means.

Optionally, a selection can also take place with respect to sensors and/or actuators 160, which can be integrated into the respective subelement. Sensors can acquire, for example, the body temperature or the heart rate and can relay them to an actuator in the form of a pacemaker, which emits electrical pulses for stimulating the cardiac muscle.

In this case, actuators are elements that convert electrical signals into mechanical or other physical variables, for example, heat or light. This can be, for example, a heating element, which regulates the temperature in a specific region of the body. Chemostats are also to be understood as actuators in the scope of the present invention. They are preferably used for regulating a pH value, an ion concentration, and/or on oxygen concentration. The actuators can be embodied in a micromechanical or micro-electromechanical construction.

Sensors that can be used in the scope of the present invention in subelements of implants and/or osteosyntheses can be, for example, chemical, electrical, electrochemical, and/or physical sensors for acquiring a patient-specific variable. Preferably used sensors are known under the term "BioMEMS". In this case, these are microelectromechanical sensors for the area of application of diagnostics and biotechnology. They preferably comprise electrochemical sensors.

Corresponding sensors in micromechanical construction as MEMS elements, which have solid-phase electrodes as reference electrodes, can be integrated into a subelement of an implant or an osteosynthesis.

Flow rate sensors are also known, which are designed as micro-electromechanical sensors. These can also be integrated into a subsegment of the implant and/or the osteosynthesis, for example, to monitor a local blood circulation.

Moreover, optical sensors, piezoresistive sensors, pressure sensors, and/or temperature sensors are known, which can preferably be embodied in micromechanical construction and which can be integrated into a subelement of an implant and/or an osteosynthesis in the scope of the present invention.

Furthermore, the implant or the osteosynthesis can also have a power supply source for the power supply of the above-mentioned actuators and/or sensors.

Furthermore, the implant or the osteosynthesis can have an analysis unit, which acquires the data ascertained by one or more sensors and possibly analyzes them or transmits them to an external computer unit, i.e., a computer unit outside the body, for further analysis, preferably by wireless data transmission. Moreover, the control unit can actuate one or more of the above-mentioned actuators as a result of the ascertained data. In one preferred variant, the control unit and the analysis unit can be implemented as one component. The control can take place both in a digital and also in an analog manner and can achieve both an interaction of subelements and also a communication with devices outside the body.

Furthermore, a selection of active ingredient and/or release systems 170 can optionally take place, with which a subelement of the implant or the osteosynthesis is coated or which are integrated or incorporated into the material of the subelement.

The term active ingredients or active ingredient systems are to be understood as pharmaceuticals. These can be, for example, antibiotics, immunosuppressive agents, growth hormones, or cytostatics.

Release systems comprise all substances that are typically additionally added to the pharmaceutical, for example, to control the release of the pharmaceutical in the body with respect to the dispensing time window and the dispensing location or to make the pharmaceutical storable under various conditions. Typical substances are, for example, tocopherol, which is often added as an antioxidant, or polysaccharides, for example, chitin, for micro-encapsulation of a corresponding pharmaceutical. The selection of the release system is also dependent, inter alia, on the selection of the material, i.e., the base material, from which the subelement is to be produced.

In a further step, the manufacturing 180 of the subelements takes place according to the above-mentioned selection criteria. The respective subelements can preferably be formed by generative manufacturing methods, for example, SLM methods, by 3D printing methods, and/or biomechanical, in particular material-removing methods, for example, milling, on the basis of the model.

The subelements can be assembled to form an implant or an osteosynthesis by an operative installation 190. In this case, the subelements of the implant or the osteosynthesis can be introduced through an operation wound into the human body in the scope of an operative intervention and assembled and/or installed in the body to form the implant or the osteosynthesis. The installation can moreover comprise the fixation of the implant, for example, on an existing skeleton.

The introduction of the subelements of the implant or the osteosynthesis enables a reduction of the dimensioning of an operation wound, and therefore the use of the implant or the osteosynthesis, which is individually adapted to the patient, can take place in the scope of a minimally-invasive procedure during operation, whereby the chances and of the period of time of a successful healing and regeneration are substantially enhanced.

The operative invention comprising the introduction of the subelements through the operation wound and the assembly thereof to form an implant or an osteosynthesis can take place endoscopically, by hand, navigated, and/or robot-assisted.

Individual examples of connections of the subelements to form an implant or an osteosynthesis are shown in detail in FIGS. 1-4. This connection preferably takes place in the body in the scope of a minimally-invasive operation.

Figure 1:
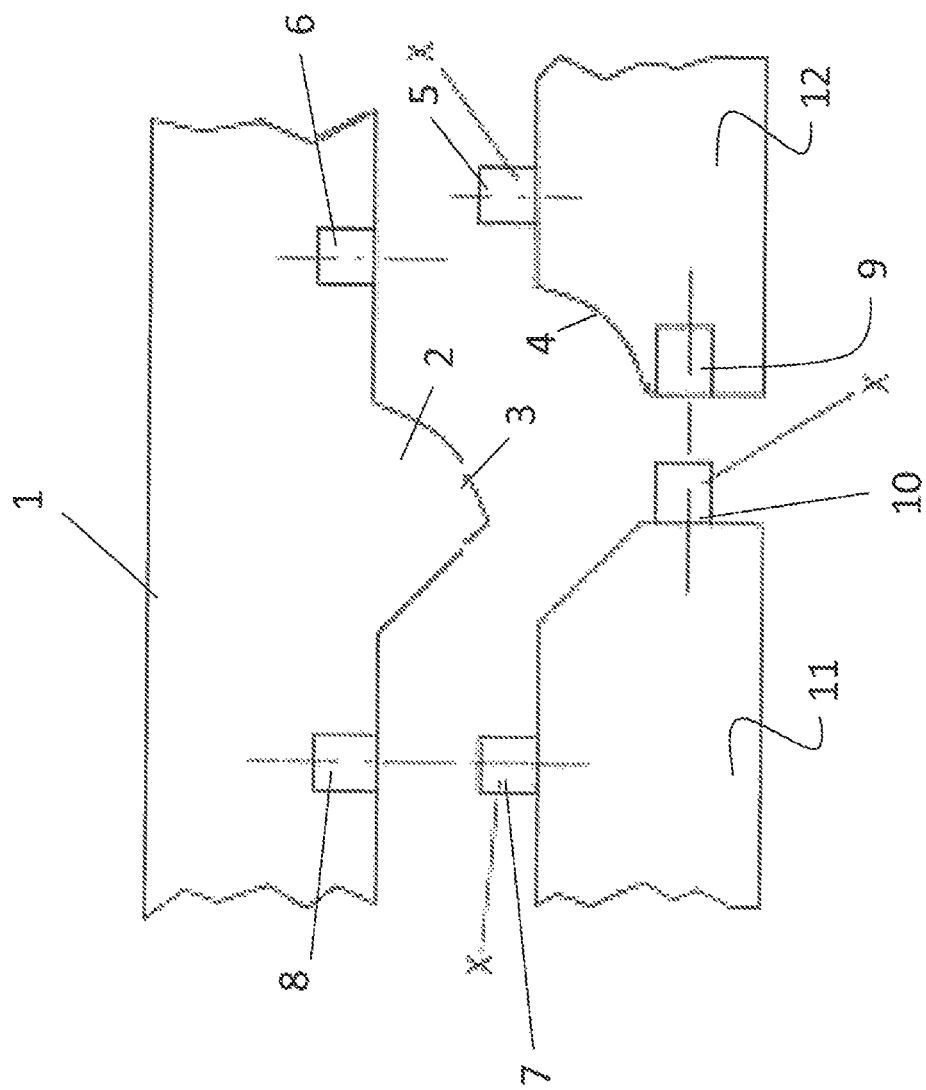
FIG. 1 shows a schematic illustration of a first connection variant between subelements of an implant or an osteosynthesis.

The subelements 1, 11, and 12 can be seen in FIG. 1. These can be, for example, bone plates made of PLA plastic in this case. They have uneven structures having projections 2 and receptacles 4, which bear on one another on the contact surfaces 3 thereof with interlocking of the subelements 1, 11, and 12.

The shape of the subelements and the material thereof can preferably be produced on the basis of a simulated load analysis. Corresponding simulation programs are commercially available and can be ascertained, for example, as a CAD system in the scope of the finite element method.

The subelements 1, 11, and 12 moreover have equivalent projections 5, 7, 10 and receptacles 6, 8, 9 to enable a friction-locked and interlocking connection in the preferred form of a plug connection, preferably in multiple spatial connections.

One or more bionic connections are also preferred as connections between subelements. This bionic connection can preferably be actuated by endogenous tissue, for example, muscles, or by nerve transmission.

Figure 2:
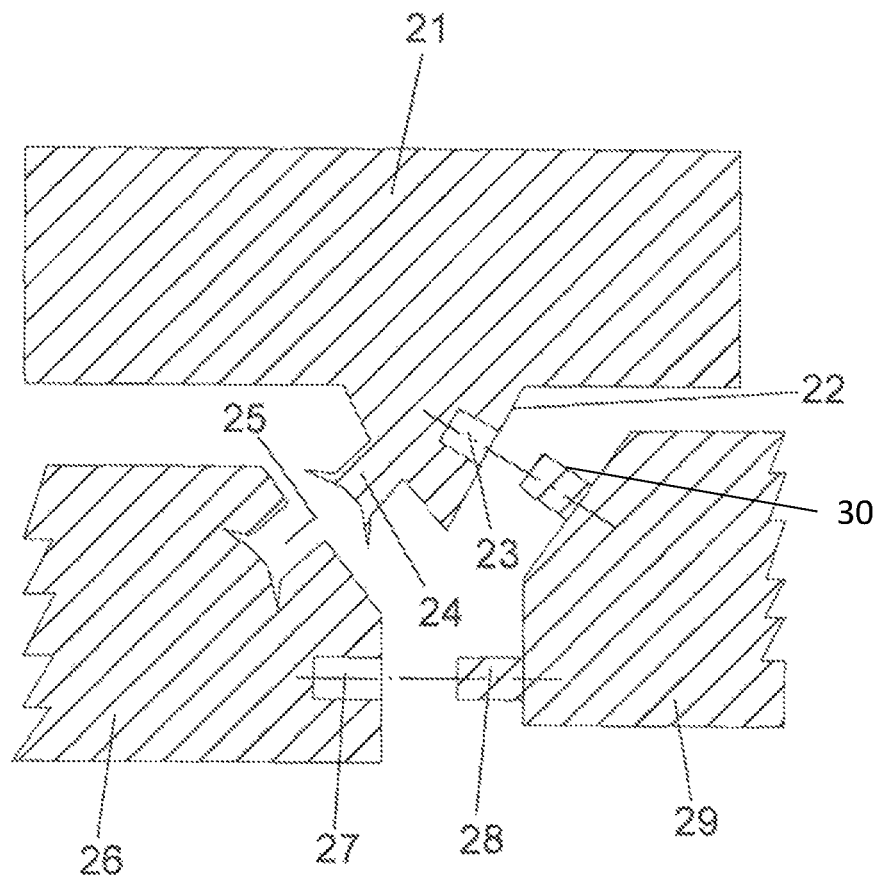
FIG. 2 shows a schematic illustration of a second connection variant between subelements of an implant or an osteosynthesis.

FIG. 2 shows different types of plug connections, whose projections and receptacles are arranged on subelements 21, 26, 29. Subelement 29 has equivalent projections 28, which protrude in different spatial directions from the subelement. Subelement 26 has two receptacles 25 and 27, which have different geometrical formations. While a first receptacle 27 is formed cylindrical, the second of the receptacles 25 has an undercut. A projection 24 of the subelement 21 engages in an interlocking and frictional-locked manner in this receptacle having undercut. This subelement 21 moreover has a receptacle 23, into which the projection 30 can be plugged in an interlocking and friction-locked manner.

Figure 3:
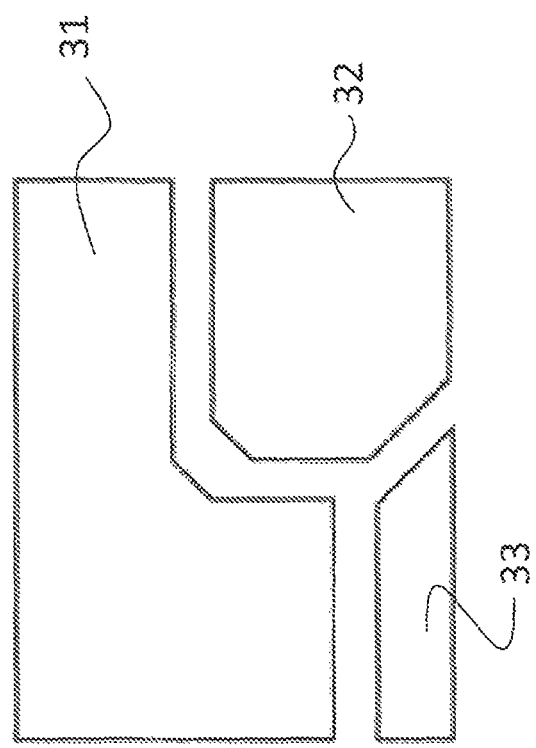
FIG. 3 shows a schematic illustration of a third connection variant between subelements of an implant or an osteosynthesis.

FIG. 3 shows three subelements 31, 32, 33. These can have magnetic material at least in some regions or can have a magnetic coating at least on some regions on the contact surfaces. Furthermore, the contact surfaces can optionally have one or more substances that connect to one another with material bonding in the body under the action of bodily fluids, and therefore a unified body is gradually formed from the subelements. Such substances can be encapsulated harmless adhesion promoters or adhesion promoter components, which are enclosed in a biodegradable encapsulation.

Figure 4:
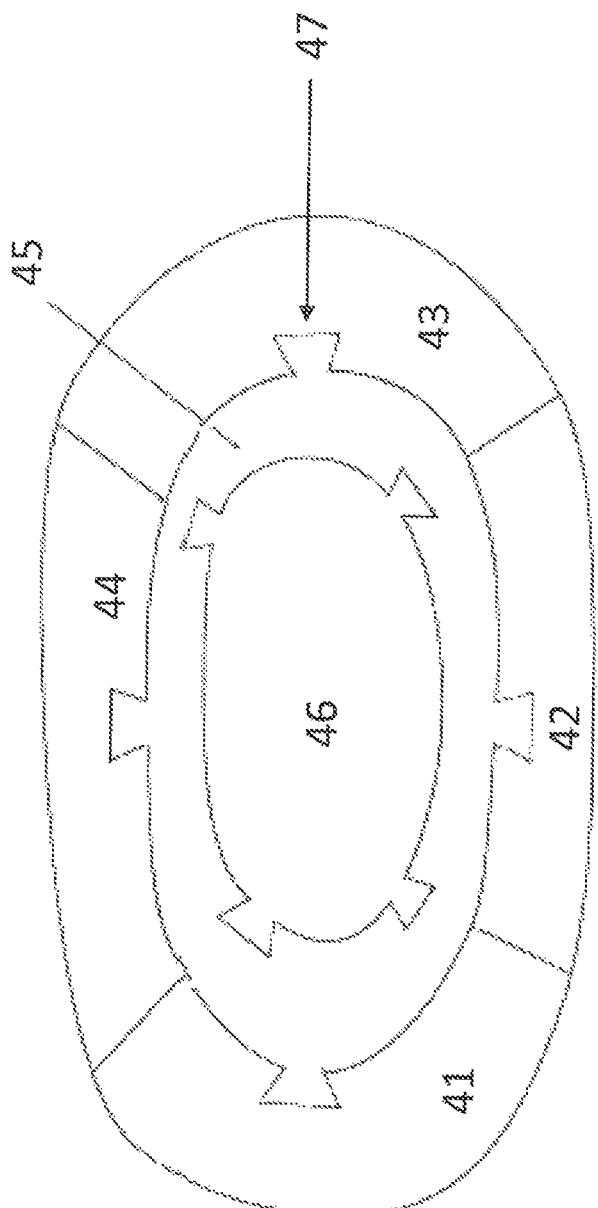
FIG. 4 shows a schematic illustration of a fourth connection variant between subelements of an implant or an osteosynthesis.

FIG. 4 shows the top view of the plate-shaped osteosynthesis. In this case, the subelements 41, 42, 43, 44, 45, 46 are formed curved and are connected to one another via a so-called dovetail connection 47.

FIGS. 1-4 only illustrate a few preferred examples of connections. However, bayonet connections or other connection variants of the subelements are also implementable in the scope of the present invention.

In one preferred embodiment of the invention, a subelement or a connection can have an intended breakpoint, in which the installed implant or the installed osteosynthesis preferably breaks in the event of stronger mechanical load.

Figure 6:
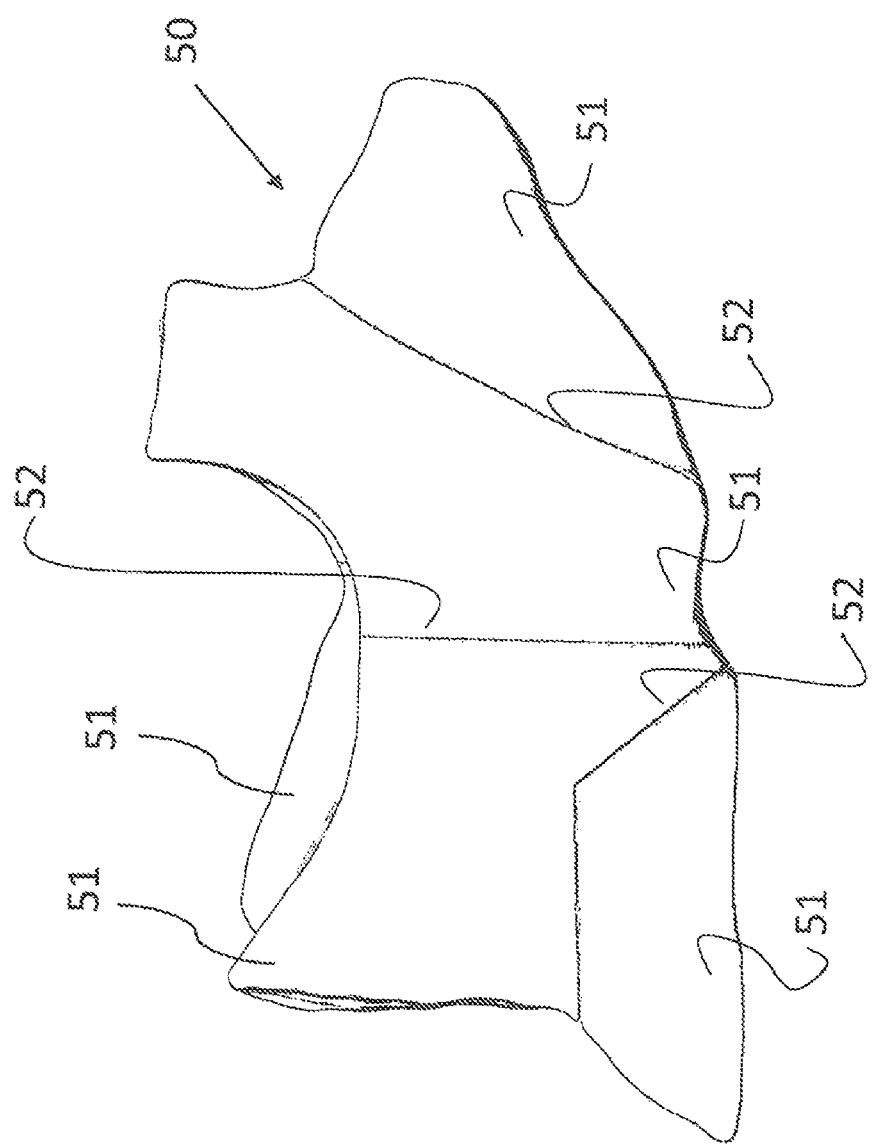
FIG. 6 shows a schematic illustration of an implant for a cheekbone in an assembled state according to the invention.
Figure 7:
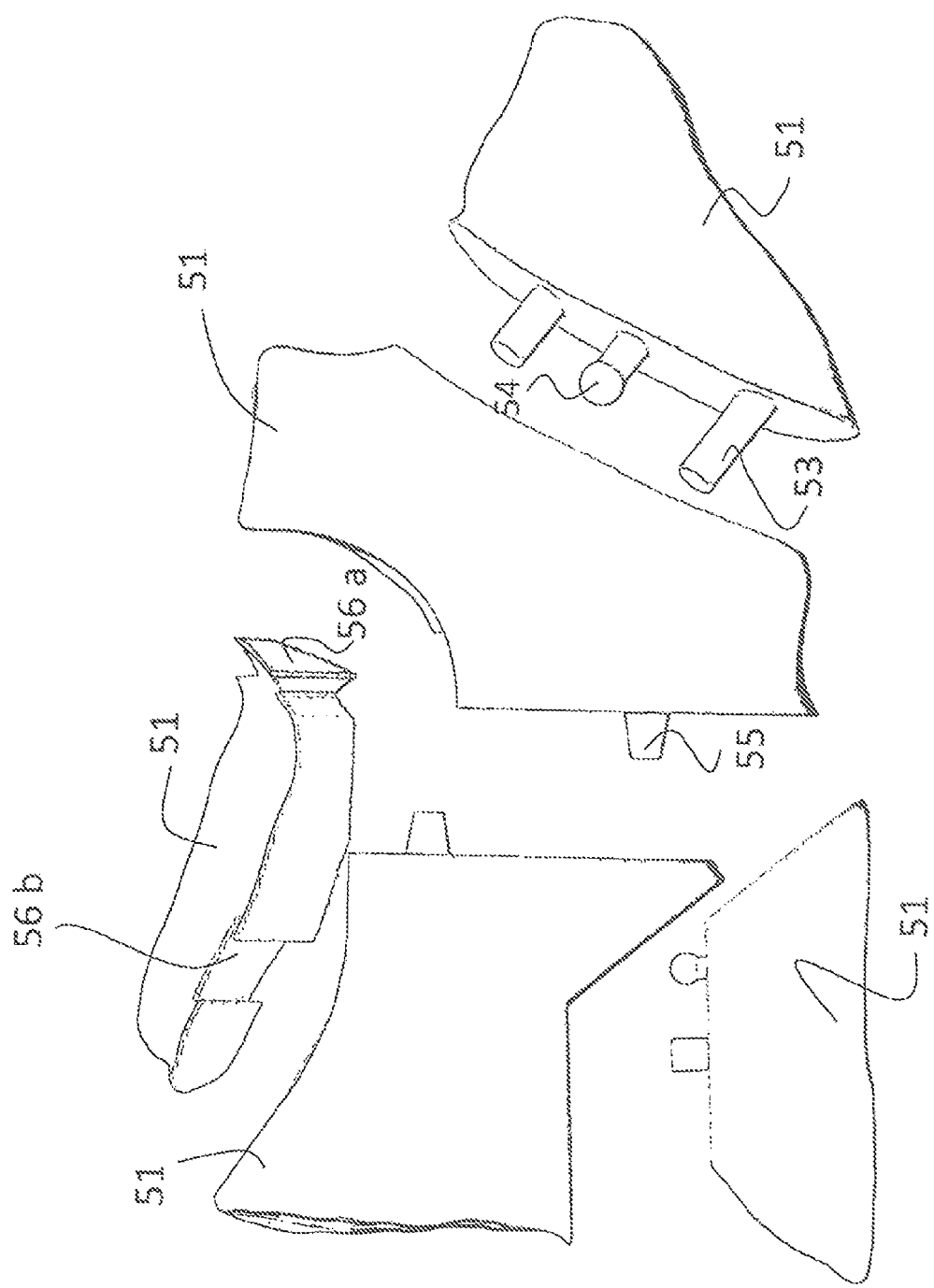
FIG. 7 shows a schematic illustration of an implant for a cheekbone in a disassembled state according to the invention.

FIGS. 6 and 7 show an example of a corresponding implant 50 for a cheekbone. In FIG. 6, the implant 50 is assembled from multiple subelements 51. The transitions 52 between the subelements can be seen clearly in this case. Each of the subelements is dimensioned differently in relation to the other subelements.

In FIG. 7, the implant is illustrated in the disassembled state. It can be seen that every transition has a different type of connection. This can be, for example, a plug connection having cylindrical plug heads 53. These enable a stability laterally in relation to the plugging direction. For better resistance against pulling apart, a plug connection having ball head 54 is recommended. A further connection variant can be a toothing 55. Finally, it can be seen that a subelement 51 is fastened on the remaining implant by means of a dovetail plug connection 56a and 56b. An eye, which only exerts a very small weight on this subelement in the plug direction, can rest on this subelement, for example. However, the dovetail plug connection 56a and 56b can resist very strong tensile forces in the direction perpendicular to the connection surfaces.

FIG. 7 shows that a force distribution on the implant, which also occurs naturally in the body on the implant, can be understood by selection of the connection types. The strength of the connection between the different subelements 51 can be selected accordingly.

The above-mentioned exemplary embodiments relate to the human body. However, it is already apparent from the context of the present invention that the invention can also be used in animals.

Although the invention has been illustrated and described in detail by way of preferred embodiments, the invention is not limited by the examples disclosed, and other variations can be derived from these by the person skilled in the art without leaving the scope of the invention. It is therefore clear that there is a plurality of possible variations. It is also clear that embodiments stated by way of example are only really examples that are not to be seen as limiting the scope, application possibilities or configuration of the invention in any way. In fact, the preceding description and the description of the figures enable the person skilled in the art to implement the exemplary embodiments in concrete manner, wherein, with the knowledge of the disclosed inventive concept, the person skilled in the art is able to undertake various changes, for example, with regard to the functioning or arrangement of individual elements stated in an exemplary embodiment without leaving the scope of the invention, which is defined by the claims and their legal equivalents, such as further explanations in the description.

The invention claimed is:

1. A method for providing subelements of a multipart implant or multipart osteosynthesis before the introduction thereof into a human and/or animal body, the method comprising:
   A) acquiring data of a patient for whom the implant or the osteosynthesis is intended using a CT scan of the patient;
   B) producing, based on the acquired data, a model of an affected organ, an affected bone, and/or surroundings of the affected organ and/or the affected bone;
   C) producing, based on the model, manufacturing specifications for at least two or more subelements configured to be assembled to form the implant or the osteosynthesis, wherein the manufacturing specifications comprise:
      C1) a dimensioning of the at least two or more subelements;
      C2) a material selection with respect to one or more materials for a respective subelement; and
      C3) a selection of one or more connection types between the respective subelements;
   D) manufacturing the subelements based on the manufacturing specifications, wherein the at least two or more subelements are configured for assembly with one another to form the implant or the osteosynthesis,
   wherein the model is produced based on the CT scan, wherein a geometry of the model including locally varying individual material thicknesses and individually-distributed material types is acquired based on the CT scan,
   wherein the subelements and connectors having the selected one or more connection types form the multipart implant or multipart osteosynthesis,
   wherein the subelements are connected to one another in a formfitting manner,
   wherein each connection type includes a projection on one of the subelements and a receptacle for the projection on a subelement adjoining the one of the subelements, and wherein the projection and receptacle engage in a friction-locked and interlocking manner,
wherein the multipart implant or multipart osteosynthesis includes at least two different connection types, and
wherein the selection of the at least two different connection types based on the model includes selecting the at least two different connection types based on transverse loading, weight per unit area, or tensile stress on a connection formed by the respective one of the at least two different connection types.

2. The method of claim 1, wherein the material selection comprises one or more of the following materials: shape-memory material, self-assembly material, gradient material, artificial muscles, tissue components, skin, mucosal membrane, periosteum, and soft tissue.

3. The method of claim 1, wherein the connection types is selected between connection types of a dovetail connection, a male connector connection, a joint connection, and a ball joint head connection.

4. The method of claim 1, wherein the production of the model is a three-dimensional computer model formed according to a finite element method.

5. The method of claim 1, wherein the acquisition of data is performed by an imaging method for the purpose of producing a three-dimensional model.

6. The method of claim 1, wherein different material parameters and material limits of subregions of the implant or the osteosynthesis are taken into consideration to produce the model.

7. The method of claim 6, wherein different material parameters and material limits include material thickness, material yield strength, material breaking point of mechanical load from different directions, and material elasticity of the subregions of the implant or the osteosynthesis.

8. The method of claim 1, wherein at least 66% of all of the at least two or more subelements, are manufactured differently dimensioned from one another.

9. The method of claim 1, wherein the at least two or more subelements, in an assembled state of the implant or the osteosynthesis, define an edge model having a greater volume than each individual subelement.

10. The method of claim 9, wherein the assembled state of the implant or the osteosynthesis, define an edge model having a volume at least eight times larger than each individual subelement.

11. The method of claim 1, wherein
a first subelement of the at least two or more subelements is manufactured from a first material or a first material combination,
a second subelement of the at least two or more subelements is manufactured from a second material or a second material combination,
a density averaged to volume or modulus of elasticity averaged to the volume of the first material or the first material combination, is greater than the density averaged to the volume or the modulus of elasticity averaged to the volume of the second material or the second material combination.

12. The method of claim 1, wherein a subelement of the at least two or more subelements is manufactured from a first material and from a second material, wherein a density or modulus of elasticity of the first material is greater than a density or modulus of elasticity of the second material.

13. The method of claim 1, wherein one or more of the at least two or more subelements consist of resorbable plastic or magnesium.

14. The method of claim 1, wherein ranges of force transmission between the projection and the receptacle of the at least two different connection types are different.

15. A method for providing subelements of a multipart implant or multipart osteosynthesis before the introduction thereof into a human and/or animal body, the method comprising:
A) acquiring data of a patient for whom the implant or the osteosynthesis is intended using a CT scan of the patient;
B) producing, based on the acquired data, a model of an affected organ, an affected bone, and/or surroundings of the affected organ and/or the affected bone;
C) producing, based on the model, manufacturing specifications for at least two or more subelements configured to be assembled to form the implant or the osteosynthesis, wherein the manufacturing specifications comprise:
C1) a dimensioning of the at least two or more subelements;
C2) a material selection with respect to one or more materials for a respective subelement; and
C3) a selection of one or more connection types between the respective subelements;
D) manufacturing the subelements based on the manufacturing specifications, wherein the at least two or more subelements are configured for assembly with one another to form the implant or the osteosynthesis,
wherein the model is produced based on the CT scan,
wherein a geometry of the model including locally varying individual material thicknesses and individually-distributed material types is acquired based on the CT scan,
wherein the subelements and connectors having the selected one or more connection types form the multipart implant or multipart osteosynthesis,
wherein the subelements are connected to one another in a formfitting manner, and
wherein each connection type includes a projection on one of the subelements and a receptacle for the projection on a subelement adjoining the one of the subelements, and wherein the projection and receptacle engage in a friction-locked and interlocking manner,
wherein the selection of the connection type of individual subelements is performed as a function of individual load cases on the at least two or more subelements on the basis of the model.

16. A method for providing subelements of a multipart implant or multipart osteosynthesis before the introduction thereof into a human and/or animal body, the method comprising:
A) acquiring data of a patient for whom the implant or the osteosynthesis is intended using a CT scan of the patient;
B) producing, based on the acquired data, a model of an affected organ, an affected bone, and/or surroundings of the affected organ and/or the affected bone;
C) producing, based on the model, manufacturing specifications for at least two or more subelements configured to be assembled to form the implant or the osteosynthesis, wherein the manufacturing specifications comprise C1) a dimensioning of the at least two or more subelements, C2) a material selection with respect to one or more materials for a respective subelement, and C3) a selection of two or more connection types between the respective subelements, and wherein the selection of the two or more connection types is produced based on the model includes selecting the at least two different connection types based on transverse loading, weight per unit area, or tensile stress on a connection formed by the respective one of the at least two different connection types;

D) manufacturing the subelements based on the manufacturing specifications, wherein the at least two or more subelements are configured for assembly with one another to form the implant or the osteosynthesis, wherein the model is produced based on the CT scan, wherein a geometry of the model including locally varying individual material thicknesses and individually-distributed material types is acquired based on the CT scan, wherein the subelements and connectors having the selected one or more connection types form the multipart implant or multipart osteosynthesis.

\* \* \* \* \*